United States Patent
Watanabe et al.

(10) Patent No.: US 7,569,016 B2
(45) Date of Patent: Aug. 4, 2009

(54) ULTRASONIC DIAGNOSTIC APPARATUS

(75) Inventors: Yoshinobu Watanabe, Yokohama (JP); Yoshinao Tannaka, Aiko-gun (JP); Takao Suzuki, Yokohama (JP); Hisashi Hagiwara, Yokohama (JP)

(73) Assignee: Panasonic Corporation, Osaka (JP)

( * ) Notice: Subject to any disclaimer, the term of this patent is extended or adjusted under 35 U.S.C. 154(b) by 583 days.

(21) Appl. No.: 10/562,550

(22) PCT Filed: Jul. 2, 2004

(86) PCT No.: PCT/JP2004/009792

§ 371 (c)(1), (2), (4) Date: Dec. 29, 2005

(87) PCT Pub. No.: WO2005/002446

PCT Pub. Date: Jan. 13, 2005

(65) Prior Publication Data
US 2008/0125651 A1    May 29, 2008

(30) Foreign Application Priority Data
Jul. 3, 2003  (JP) .............................. 2003-191310

(51) Int. Cl.
*A61B 8/00* (2006.01)
(52) U.S. Cl. ....................... 600/438; 600/437; 600/454; 600/481; 382/128
(58) Field of Classification Search .................. 600/437
See application file for complete search history.

(56) References Cited
U.S. PATENT DOCUMENTS
4,217,909 A * 8/1980 Papadofrangakis et al. .. 600/441

(Continued)

FOREIGN PATENT DOCUMENTS
JP      2889568      2/1999

(Continued)

OTHER PUBLICATIONS

Hasegawa et al., "*Automatic Detection of Lumen-Intima Boundary of Posterior Wall of Carotid Artery*", The Institute of Electronics, Information and Communication Engineers, Technical Report of IEICE, US2003-16, pp. 5-10 (2003).

(Continued)

*Primary Examiner*—Brian Casler
*Assistant Examiner*—Parikha S Mehta
(74) *Attorney, Agent, or Firm*—Hamre, Schumann, Mueller & Larson, P.C.

(57) ABSTRACT

There are provided transmission means (1) for transmitting an ultrasonic signal from a surface of a skin of a subject toward a blood vessel (21) of the subject, reception means (3) for receiving a reflected ultrasonic echo and converting the ultrasonic echo into an electric signal to obtain the ultrasonic echo signal in a depth direction from the surface of the skin, movement detection means (5) for analyzing a phase of the ultrasonic echo signal in a direction traversing the blood vessel to calculate a movement amount in each of a plurality of regions including a blood vessel wall and a vicinity of the blood vessel wall, analysis means (7) for analyzing a state of the blood vessel based on a variation in the calculated movement amount in each of the regions, boundary position detection means (8) for detecting a boundary position between the blood vessel wall and a blood flow region of the blood vessel based on a result of the analysis by the analysis means, and stability judgment means (15) for comparing the detected boundary position with a detection result in a previous cycle.

18 Claims, 5 Drawing Sheets

U.S. PATENT DOCUMENTS

| | | | |
|---|---|---|---|
| 4,688,428 A * | 8/1987 | Nicolas | 73/602 |
| 5,220,923 A * | 6/1993 | Hagiwara et al. | 600/455 |
| 5,415,172 A * | 5/1995 | Tannaka et al. | 600/437 |
| 5,840,028 A * | 11/1998 | Chubachi et al. | 600/437 |
| 6,132,373 A | 10/2000 | Ito et al. | |
| 6,176,832 B1 | 1/2001 | Habu et al. | |
| 6,258,031 B1 * | 7/2001 | Sunagawa et al. | 600/443 |
| 6,770,034 B2 * | 8/2004 | Sunagawa et al. | 600/443 |
| 2003/0009101 A1 * | 1/2003 | Sunagawa et al. | 600/437 |
| 2003/0199762 A1 * | 10/2003 | Fritz et al. | 600/437 |
| 2004/0260180 A1 * | 12/2004 | Kanai et al. | 600/449 |
| 2007/0123777 A1 * | 5/2007 | Watanabe et al. | 600/437 |

FOREIGN PATENT DOCUMENTS

| | | |
|---|---|---|
| JP | 11-76233 | 3/1999 |
| JP | 2000-229078 | 8/2000 |
| JP | 2000-271117 | 10/2000 |
| JP | 2003-126090 | 5/2003 |

OTHER PUBLICATIONS

Umezawa et al., *"Measurement of local pulse wave velocity for evaluation of viscoelasticity from small vibrations on artery measured using ultrasound"*, The Institute of Electronics, Information and Communication Engineers, Technical Report of IEICE, EA99-42, pp. 17-23 (1999).

Hasegawa et al., *"Evaluation of Regional Elastic Modulus of Cylindrical Shell with Nonuniform Wall Thickness"*, J Med Ultrasonics, vol. 28, No. 1, pp. J3-J13 (2001).

* cited by examiner

ULTRASONIC DIAGNOSTIC APPARATUS

TECHNICAL FIELD

The present invention relates to an ultrasonic diagnostic apparatus having a function of determining a state of a blood vessel by ultrasonic waves.

BACKGROUND ART

It is known as a function of ultrasonic diagnostic apparatuses that ultrasonic pulses are transmitted from a surface of a skin of a subject toward a blood vessel of the subject, so as to carry out a measurement on various states of the blood vessel based on ultrasonic echo signals reflected by the blood vessel.

For example, a method of detecting the boundary of a blood vessel wall by ultrasonic waves is disclosed in JP 2000-271117 A. According to this method, assuming that a blood vessel has a standard structure, the displacement and diameter of a blood vessel, the thickness of a blood vessel wall, and the like are measured based on a maximum peak value and a second peak value of a luminance signal in image data obtained based on ultrasonic waves reflected by the blood vessel.

Further, a method of calculating a propagation speed of pulse waves in a blood vessel is disclosed in JP 11 (1999)-76233 A. According to this method, a propagation speed of pulse waves is determined based on a variation with time in the cross-sectional shape of a blood vessel in a plurality of regions in a longitudinal direction of the blood vessel.

Further, Japanese Patent No. 2889568 discloses a method of detecting an IMT (Intima-Media Thickness) value of a blood vessel wall (carotid artery) by ultrasonic waves. According to this method, assuming that a blood vessel has a standard structure, an IMT value of a blood vessel wall (carotid artery) is measured based on a maximum peak value and a second peak value of a luminance signal in image data obtained based on ultrasonic waves reflected by the blood vessel.

However, in an actual medical diagnosis of a blood vessel, it is difficult in many cases to carry out a measurement in a stable state due to a variety of factors such as a state in which an ultrasonic probe is fixed, a stationary and respiratory state of a subject, and the like.

On this account, in an actual measurement, a large-scale device is used to fix a probe and a subject and the subject is requested to stop his/her breathing during the measurement, so that a measurement is more likely to be carried out stably. Further, the measurement is carried out a plurality of times and data that can be measured with accuracy are selected. Consequently, the measurement takes a long diagnosis time, and a constant measurement accuracy cannot be obtained by different operators. Also, for future use in the area of a diagnosis targeted for a large number of people, such as a medical examination, means for judging a state of stability of a measurement is being demanded.

DISCLOSURE OF INVENTION

An object of the present invention is to provide an ultrasonic diagnostic apparatus that is capable of judging a state of stability of a measurement.

An ultrasonic diagnostic apparatus according to the present invention includes: transmission means for transmitting at least one ultrasonic signal from a surface of a skin of a subject toward a blood vessel of the subject; reception means for receiving an ultrasonic echo reflected by the blood vessel and converting the ultrasonic echo into an electric signal to obtain the ultrasonic echo signal in a depth direction from the surface of the skin; movement detection means for analyzing a phase of the ultrasonic echo signal in a direction traversing the blood vessel to calculate a movement amount in each of a plurality of regions including a blood vessel wall composing the blood vessel and a vicinity of the blood vessel wall; analysis means for analyzing a state of the blood vessel based on a variation in the calculated movement amount in each of the regions; boundary position detection means for detecting a boundary position between a blood flow region and the blood vessel wall of the blood vessel based on a result of the analysis by the analysis means; and stability judgment means for comparing the boundary position detected by the boundary position detection means with a detection result in a previous cycle.

This configuration makes it possible to judge the stability of the detection of the boundary position based on a result of comparing the detected boundary position between the blood flow region and the blood vessel wall with a detection result in a previous cycle. Consequently, an operator easily and promptly can be notified whether measured data are appropriate or not during a measurement.

Preferably, the above-mentioned configuration further includes an ROI (Region of Interest) positioning means for positioning an ROI where the boundary position in the depth direction from the surface of the skin is to be detected by the boundary position detection means, and the ROI positioning means positions the ROI so that the ROI lies astride at least one of an anterior wall of the blood vessel wall on a side closer to the transmission means and a posterior wall of the blood vessel wall on a side farther from the transmission means. This configuration allows reliable detection of the boundary position between the blood vessel wall and the blood flow region.

Preferably, the transmission means transmits a plurality of ultrasonic signals toward a plurality of regions in a longitudinal direction of the blood vessel, the boundary position detection means detects the plurality of boundary positions in the longitudinal direction of the blood vessel, and the stability judgment means compares the plurality of boundary positions detected by the boundary position detection means, thereby judging the stability of a result of the detection of the boundary positions. This configuration allows the judgment accuracy to be increased.

In the above-mentioned configuration, the boundary position detection means can detect the plurality of boundary positions in the depth direction from the surface of the skin, and a blood vessel diameter calculation means for calculating a diameter of the blood vessel based on the plurality of detected boundary positions further can be included. This configuration allows multifaceted detection of a state of the blood vessel.

The stability judgment means can compare the diameter of the blood vessel calculated by the blood vessel diameter calculation means with a calculation result in a previous cycle, thereby judging the stability of a result of the detection of the boundary positions. This configuration allows stable detection of a state of the blood vessel.

The boundary position detection means can detect the boundary positions in the plurality of regions in the longitudinal direction of the blood vessel, and a pulse wave propagation speed calculation means for calculating a pulse wave propagation speed indicating a speed at which a pulse wave propagates, based on a variation with time in the plurality of boundary positions detected by the boundary position detection means further can be included. This configuration allows multifaceted detection of a state of the blood vessel.

The stability judgment means can compare the pulse wave propagation speed calculated by the pulse wave propagation speed calculation means with the pulse wave propagation speed calculated in a previous cycle, thereby judging the stability of a result of the calculation of the pulse wave propagation speed. This configuration allows stable detection of the pulse wave propagation speed.

The pulse wave propagation speed calculation means can calculate pulse wave propagation speeds in a plurality of adjacent regions in the longitudinal direction of the blood vessel, and the stability judgment means can compare the pulse wave propagation speeds in the plurality of adjacent regions, thereby judging the stability of the calculation of the pulse wave propagation speeds by the pulse wave propagation speed calculation means. This configuration allows the judgment accuracy to be increased.

The boundary position detection means can detect a boundary position between a tunica intima and the blood flow region of the blood vessel and a position of a tunica media of the blood vessel based on a hardness value of tissue in the depth direction, and the stability judgment means can compare the boundary position and the position of the tunica media detected by the boundary position detection means with the boundary position and the position of the tunica media calculated a predetermined number or more of cycles prior to the present cycle, thereby judging the stability of a result of the detection of the boundary position and the position of the tunica media. This configuration allows stable detection of the boundary position and the position of the tunica media.

The transmission means can transmit a plurality of ultrasonic signals toward a plurality of regions in the longitudinal direction of the blood vessel, the boundary position detection means can detect the boundary positions between the tunica intima and the blood flow region of the blood vessel and the positions of the tunica media of the blood vessel in a plurality of regions adjacent to each other in the longitudinal direction of the blood vessel, and the stability judgment means can compare the boundary positions and the positions of the tunica media adjacent to each other that are detected by the boundary position detection means, thereby judging the stability of the detection of the boundary positions and the positions of the tunica media by the boundary position detection means. This configuration allows stable detection of the boundary position and the position of the tunica media.

An IMT (Intima-Media Thickness) calculation means for measuring an IMT, which is a thickness from the tunica intima to the tunica media, based on a variation with time in the boundary position between the tunica intima and the blood flow region of the blood vessel and a variation with time in the position of the tunica media of the blood vessel further can be included, and the stability judgment means can judge the stability of a result of the detection of the boundary position by the boundary position detection means based on the IMT measured by the IMT calculation means. This configuration allows stable detection of the boundary position.

The IMT calculation means can calculate the IMT values in a plurality of regions adjacent to each other in the longitudinal direction of the blood vessel, and the stability judgment means can compare the IMT values in the plurality of regions, thereby judging the stability of a result of the detection of the boundary position by the boundary position detection means. This configuration allows stable detection of the boundary position.

Display means for displaying the stability judged by the stability judgment means further can be included. This configuration allows visual recognition of the stability.

DESCRIPTION OF THE INVENTION

Hereinafter, embodiments of the present invention will be described with reference to the drawings.

First Embodiment

Figure 1:
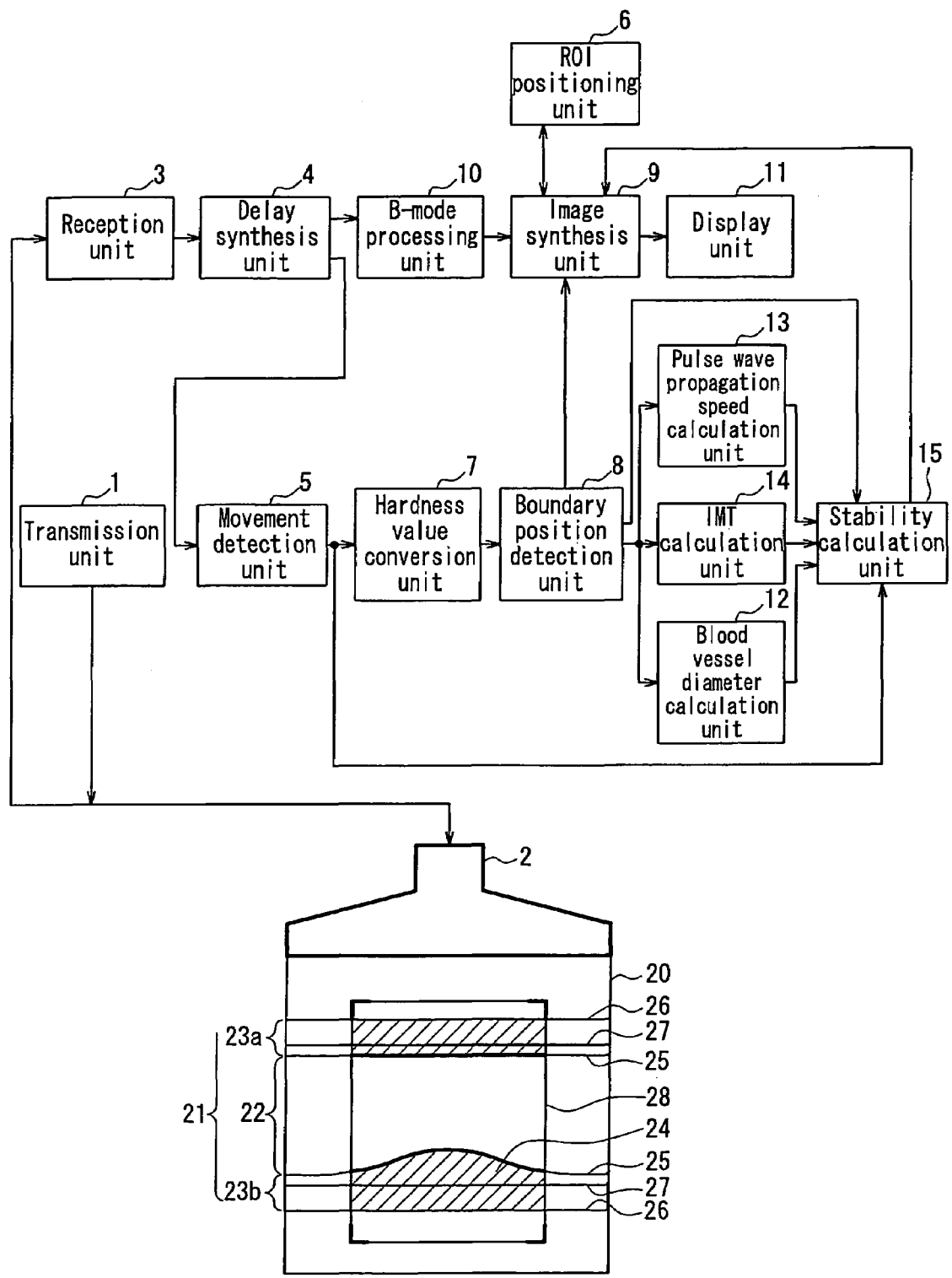
FIG. 1 is a block diagram showing a configuration of an ultrasonic diagnostic apparatus according to a first embodiment of the present invention.

FIG. 1 is a block diagram schematically showing a configuration of an ultrasonic diagnostic apparatus according to a first embodiment of the present invention. Note here that FIG. 1 also shows a B-mode image 20 received by the ultrasonic diagnostic apparatus. A transmission unit 1 generates an ultrasonic pulse and supplies it to an ultrasonic probe 2. The ultrasonic probe 2 transmits the ultrasonic pulse supplied from the transmission unit 1 from a surface of a skin of a living body toward the inside thereof. The B-mode image 20 is an image obtained when the ultrasonic pulse is transmitted toward a blood vessel 21.

In this image, the blood vessel 21 extends in a direction tilted with respect to the surface of the skin and is indicated by an anterior wall 23a and a posterior wall 23b that surround a blood flow region 22 in the lumen in which blood flows. The anterior wall 23a is a blood vessel wall on a side closer to the ultrasonic probe 2, and the posterior wall 23b is a blood vessel wall on a side farther from the ultrasonic probe 2. In this example, the blood vessel 21 has an atheroma 24 as a local disease that is developed on an inner surface of the posterior wall 23b.

The blood vessel wall shown as the anterior wall 23a and the posterior wall 23b includes a tunica intima 25 that is formed on an inner surface of the blood vessel wall and faces the blood flow region 22, a tunica adventitia 26 formed on an outer surface of the blood vessel wall, and a tunica media 27 formed between the tunica intima 25 and the tunica adventitia 26. In FIG. 1, the atheroma 24 as a local disease is developed between the tunica intima 25 and the tunica media 27.

An ultrasonic echo reflected by the blood vessel 21 is converted into an electric signal by the ultrasonic probe 2, and the obtained ultrasonic echo signal is supplied to a movement detection unit 5 on one hand via a reception unit 3 and a delay synthesis unit 4. The movement detection unit 5 detects a movement amount in each region in a depth direction from the surface of the skin based on the received ultrasonic echo signal. The detection of a movement amount in each region by the movement detection unit 5 can be carried out by a well-known method based on a phase change of the received signal, and thus a specific description will be omitted.

In the B-mode image 20, an ROI (Region of Interest) 28 is shown that is provided for detecting a boundary position in the depth direction from the surface of the skin. The positioning of the ROI 28 in a tomographic image is set by an ROI positioning unit 6. In order to achieve the object of the present embodiment, the ROI 28 is set so as to lie astride at least one of the anterior wall 23a and the posterior wall 23b. In the example shown in FIG. 1, the ROI 28 is positioned so as to lie astride both the anterior wall 23a and the posterior wall 23b.

The movement amount detected by the movement detection unit 5 is supplied to a hardness value conversion unit 7. The hardness value conversion unit 7 converts the movement amount detected by the movement detection unit 5 into a hardness value of tissue in the depth direction from the surface of the skin. For example, when a difference in the movement amount (thickness variation) between neighboring regions is analyzed from a variation in the movement amount in respective regions of the blood vessel wall, a large thickness variation is obtained in a soft region, while a small thickness variation is obtained in a hard region. Thus, based on this, the hardness value in each region can be detected. The hardness value of the tissue obtained by the hardness value conversion unit 7 is supplied to a boundary position detection unit 8.

The boundary position detection unit 8 detects a boundary position between the tunica intima 25 and the blood flow region 22 of the blood vessel 21 and a position of the tunica media 27 based on the hardness value. Since the detection is carried out based on the hardness value of the tissue in the depth direction, by which a variation state of the tissue is clarified, the boundary position can be recognized automatically with a simple algorithm. Further, the boundary position detection unit 8 generates a two-dimensionally mapped color display image showing a cross section of the blood vessel 21, and supplies it to an image synthesis unit 9.

Instead of the hardness value conversion unit 7, a method of analyzing another state of the blood vessel based on the movement amount detected by the movement detection unit 5 may be used, so that the boundary position detection unit 8 can detect the boundary position based on a result of that analysis. For example, when attention is given to a variation state (track) of the movement amount of the blood vessel in one heartbeat, the track has different characteristics such as a movement direction reversed between the blood flow region 22 and the posterior wall 23b. Thus, by analyzing this, a middle point at which the track is reversed can be judged as the boundary position.

The received signal that has passed through the reception unit 3 and the delay synthesis unit 4 is supplied also to a B-mode processing unit 10 on the other hand. The B-mode processing unit 10 generates image information showing the cross section of the blood vessel 21 based on the received signal, and supplies it to the image synthesis unit 9. The image synthesis unit 9 synthesizes the image information supplied from the B-mode processing unit 10 and the boundary information recognized automatically by the boundary position detection unit 8, and displays the synthesis on a monitor of a display unit 11.

The detection signal from the boundary position detection unit 8 is supplied also to a blood vessel diameter calculation unit 12, a pulse wave propagation speed calculation unit 13, an IMT calculation unit 14, and a stability judgment unit 15.

The blood vessel diameter calculation unit 12 calculates a diameter of the lumen of the blood vessel 21 based on a plurality of boundary positions recognized automatically by the boundary position detection unit 8. The pulse wave propagation speed calculation unit 13 calculates a pulse wave propagation speed indicating a speed at which a pulse wave propagates, based on a variation with time in the plurality of boundary positions recognized automatically by the boundary position detection unit 8. More specifically, the boundary position detection unit 8 detects the boundary positions in a plurality of regions in a longitudinal direction of the blood vessel, and supplies them to the pulse wave propagation speed calculation unit 13. The pulse wave propagation speed calculation unit 13 calculates a pulse wave propagation speed based on a variation with time in the plurality of boundary positions. A specific method of the calculation is disclosed in JP 11 (1999)-76233 A.

The IMT calculation unit 14 uses the detection signal output from the boundary position detection unit 8 to measure the thickness of the tunica media 27 as an IMT value based on a variation with time in the boundary position between the tunica intima 25 and the blood flow region 22 and a variation with time in the position of the tunica media 27 in one heartbeat cycle. The IMT calculation unit 14 calculates at least one of a maximum value, a minimum value, and an average value of the IMT value in one heartbeat cycle.

The outputs from the blood vessel diameter calculation unit 12, the pulse wave propagation speed calculation unit 13, and the IMT calculation unit 14 are supplied to a stability judgment unit 15. The stability judgment unit 15 has a function of judging the stability of a measurement. The stability judgment unit 15 is supplied with the detection signals from the movement detection unit 5 and the boundary position detection unit 8 and judges the stability based on those signals. For example, the stability judgment unit 15 compares the movement amount of the blood vessel wall calculated by the movement detection unit 5 with the movement amount of the blood vessel wall calculated a predetermined number or more of cycles prior to the present cycle, thereby judging the stability of the result of the detection of the movement amount of the blood vessel wall by the movement detection unit 5. A detailed operation thereof will be described later.

Figure 2:
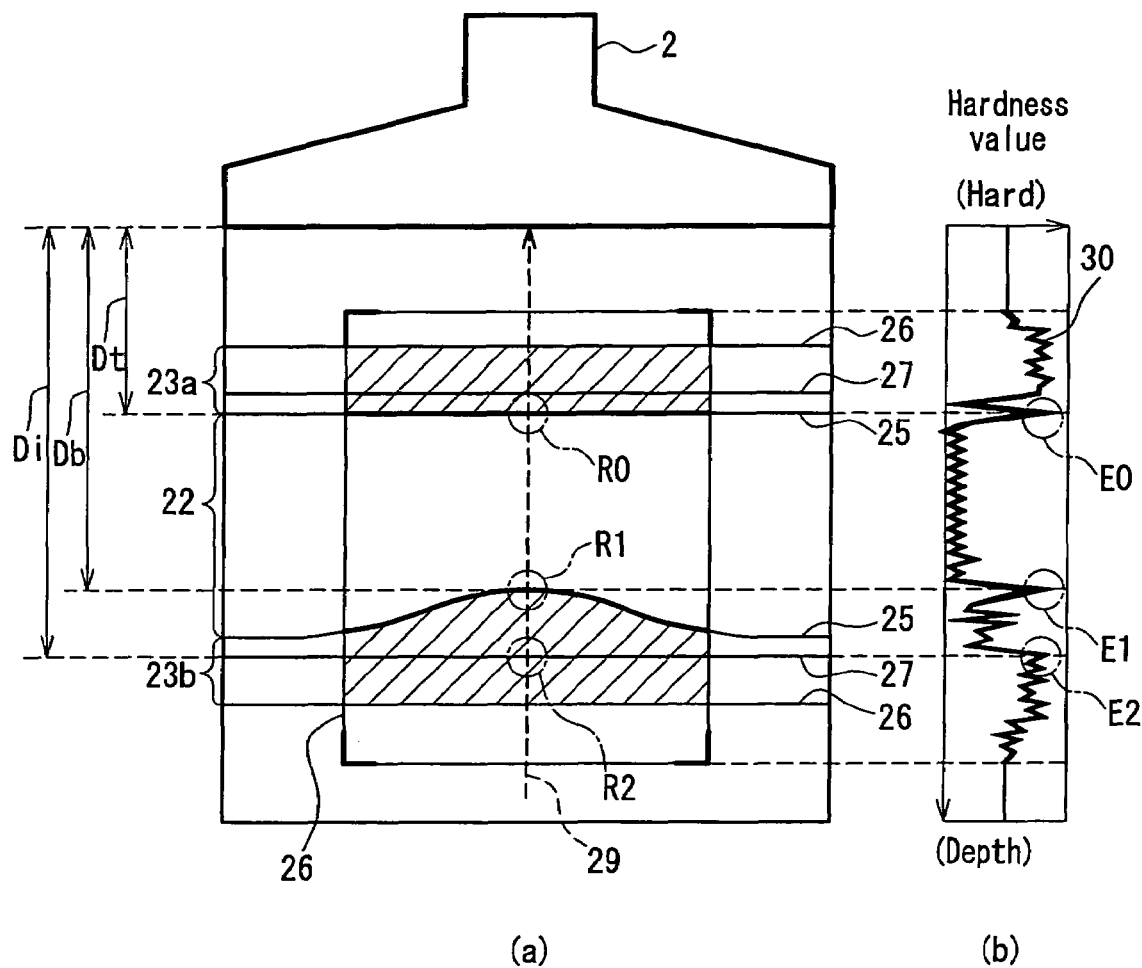
FIG. 2 is a schematic view for explaining an operation of the ultrasonic diagnostic apparatus shown in FIG. 1.

FIG. 2 is a schematic view for explaining an operation of the ultrasonic diagnostic apparatus according to the present embodiment. In FIG. 2, (a) shows an image that is the same as the B-mode image 20 shown in FIG. 1. Reference numeral 29 denotes a single scanning line indicating a track of an ultrasonic wave transmitted from the ultrasonic probe 2. In the figure, (b) shows a hardness value 30 of the tissue that is obtained by the hardness value conversion unit 7 for each portion on the scanning line 29.

Herein, attention is given to a point R0 on the tunica intima 25 of the anterior wall 23a on a side closer to the surface of the skin, a point R1 on the tunica intima 25 of the posterior wall 23b on a side farther from the surface of the skin, and a point R2 on the tunica media 27 of the posterior wall 23b on the scanning line 29. The point R0 is located at a position at a depth Dt from the surface of the skin, the point R1 is located at a position at a depth Db from the surface of the skin, and the point R2 is located at a position at a depth Di from the surface of the skin. The hardness value at the points R0, R1, and R2 is represented by E0, E1, and E2, respectively, in (b).

The hardness value 30 in the depth direction from the surface of the skin is far lower in the blood flow region 22 than on the blood vessel wall. On this account, based on the hardness value 30, the boundary position between the blood flow region 22 and the tunica intima 25 easily can be recognized automatically with a simple algorithm.

In addition, the inner diameter of the blood vessel can be calculated by the following Formula (1), and the IMT value can be calculated automatically by incorporating the following Formula (2) into an algorithm.

Inner diameter of blood vessel=$Db-Dt$ (1)

$IMT=Di-Db$ (2)

Herein, Di–Db corresponds to the thickness from the tunica intima 25 to the tunica media 27.

Further, when the transmission unit 1 transmits a plurality of ultrasonic signals toward a plurality of regions in the longitudinal direction of the blood vessel 21, and the same processing as above is performed with respect to a plurality of scanning lines 29 corresponding to a plurality of ultrasonic echo signals, it is possible to obtain distributions of the propagation speed of a pulse wave, the hardness value, and the like in the longitudinal direction of the blood vessel 21.

Next, the operation of the stability judgment unit 15 will be described with reference to FIG. 3. As mentioned above, in an actual medical diagnosis of a blood vessel, it is difficult to carry out a measurement in a stable state due to a variety of factors such as a state in which the ultrasonic probe 2 is fixed, a stationary and respiratory state of a subject, and the like. Consequently, in reality a large-scale device is used to fix the probe 2 and a subject and the subject is requested to stop his/her breathing during a measurement, so that a measurement is more likely to be carried out stably. Further, the measurement is carried out a plurality of times and data that can be measured with accuracy are selected. As a result, the measurement takes a long diagnosis time, and moreover a constant measurement accuracy cannot be obtained by different operators.

When ideal measured data are obtained in a state in which the positional relationship between a subject and the ultrasonic probe 2 is constant or a state in which the subject is in a stable state by stopping his/her breathing, the blood vessel wall has a closely analogous movement track during each heartbeat. Based on this, the stability of the measurement for detecting the IMT value itself is judged.

Figure 3:
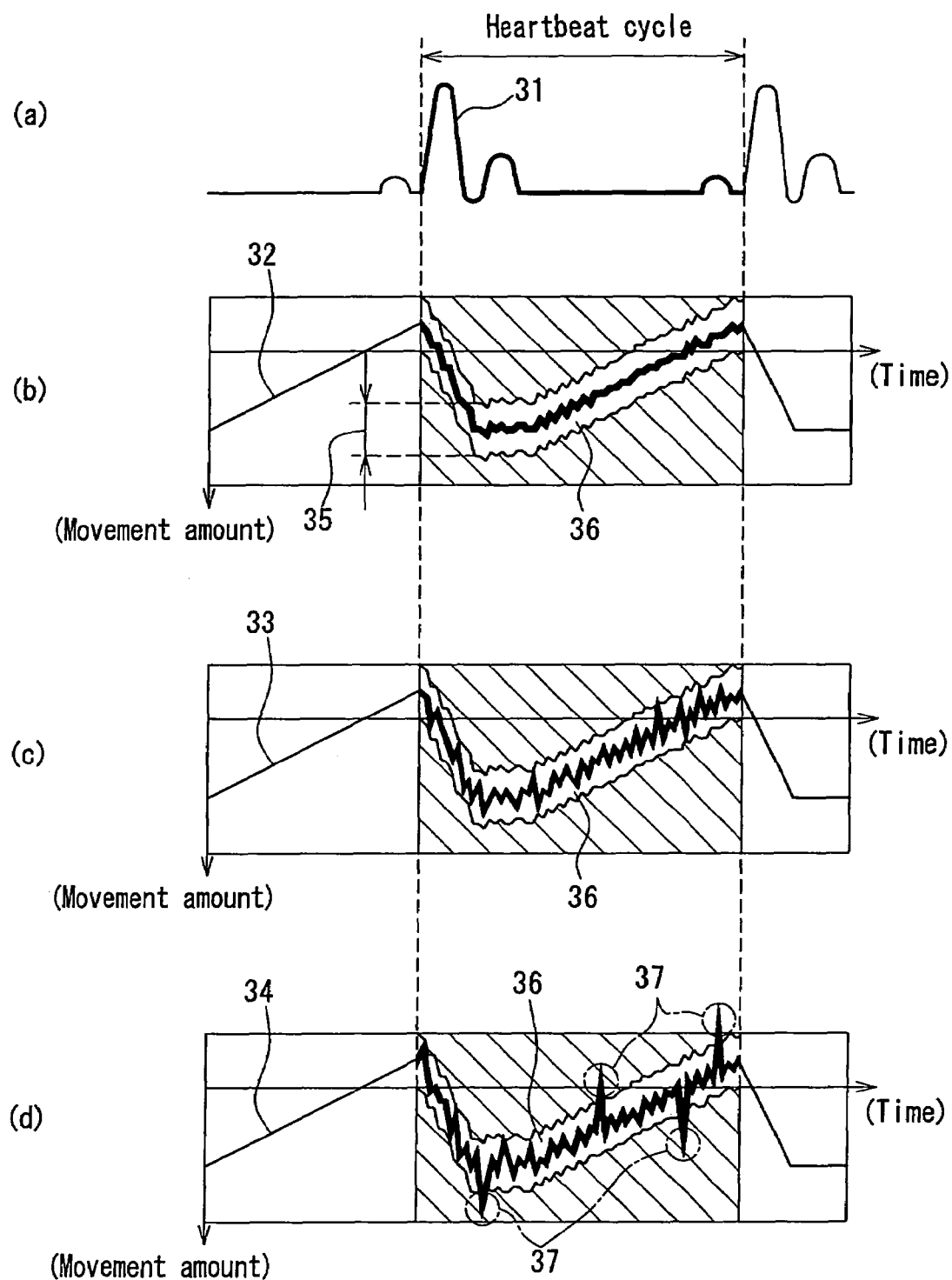
FIG. 3 is a schematic view for explaining another operation of the ultrasonic diagnostic apparatus shown in FIG. 1.

FIG. 3 is a schematic view for explaining the operation of the stability judgment unit 15. In the figure, (a) shows an ECG (Electrocadiograph) waveform 31. Waveforms shown in (b) to (d) indicate movement tracks 32, 33, and 34, respectively, of the blood vessel wall in respective measuring cycles synchronized with a heartbeat cycle of the ECG waveform 31 shown in (a). The movement track 32 shown in (b) is measured in a cycle immediately preceding the cycles in which the movement tracks 33 and 34 shown in (c) and (d) are measured.

In (b) of FIG. 3, a tolerance 36 is shown that allows for a permissible error 35 with respect to the movement track 32 in the immediately preceding cycle. The tolerance 36 is compared with a movement track in the subsequent measuring cycle. For example, in the case of the movement track 33 shown in (c) that is within the tolerance 36 at any points, it is judged that a stable measurement has been carried out. In the case of the movement track 34 shown in (d) that has improper points 37 out of the tolerance 36, it is judged that a measurement has been carried out unstably.

When an operator is notified of information indicating whether a measurement has been carried out stably or unstably in real time, the operator can judge during the measurement whether the present measurement result is reliable or not. Consequently, a measuring time can be made shorter.

Further, the stability judgment unit 15 can compare the boundary position between the blood flow region 22 and the tunica intima 25 and the position of the tunica media 27 that are detected by the boundary position detection unit 8 with the boundary position and the position of the tunica media 27 calculated a predetermined number or more of cycles prior to the present cycle, thereby judging the stability of the result of the detection of the boundary position and the position of the tunica media 27.

Further, the stability judgment unit 15 may judge whether a measurement has been carried out stably or unstably based on a difference between the measurement result in the present cycle and that in the immediately preceding cycle. Alternatively, the stability judgment unit 15 may judge whether a measurement has been carried out stably or unstably based on a comparison with stable movement tracks measured not only in the immediately preceding cycle but also in a plurality of past cycles. Further, the threshold value (permissible error 35) for the judgment as to whether a measurement has been carried out stably or unstably may be changed.

Further, the boundary position detection unit 8 can detect a plurality of boundary positions in the longitudinal direction of the blood vessel 21, and the stability judgment unit 15 can compare the plurality of boundary positions detected by the boundary position detection unit 8, thereby judging the stability of the result of the detection of the boundary positions.

In the present embodiment, the stability judgment unit 15 also can judge the stability of a measurement based on the output from the blood vessel diameter calculation unit 12, the pulse wave propagation speed calculation unit 13, or the IMT calculation unit 14 in the following manner. For example, the stability judgment unit 15 compares the diameter of the blood vessel calculated by the blood vessel diameter calculation unit 12 with a calculation result in a previous cycle, thereby judging the stability of the result of the detection of the boundary position between the blood flow region 22 and the tunica intima 25. Alternatively, the stability judgment unit 15 compares the pulse wave propagation speed calculated by the pulse wave propagation speed calculation unit 13 with that calculated in a previous cycle, thereby judging the stability of the result of the calculation of the pulse wave propagation speed. Alternatively, the pulse wave propagation speed calculation unit 13 calculates pulse wave propagation speeds in a plurality of adjacent regions in the longitudinal direction of the blood vessel 21, and the stability judgment unit 15 compares the pulse wave propagation speeds in the plurality of adjacent regions, thereby judging the stability of the result of the calculation of the pulse wave propagation speeds. Alternatively, the IMT calculation unit 14 calculates IMT values in a plurality of regions adjacent to each other in the longitudinal direction of the blood vessel 21, and the stability judgment unit 15 compares the IMT values in the plurality of regions, thereby judging the stability of the result of the detection of the boundary position by the boundary position detection unit 8.

Further, the stability judgment unit 15 may compare a value of, for example, pseudo boundary judgment position, which is obtained from an echo brightness value unsuitable for judging a boundary, in the present cycle with that in the immediately preceding cycle. By combining a plurality of such functions of judging the measurement stability, the reliability of a measurement result can be increased further.

Second Embodiment

Figure 4:
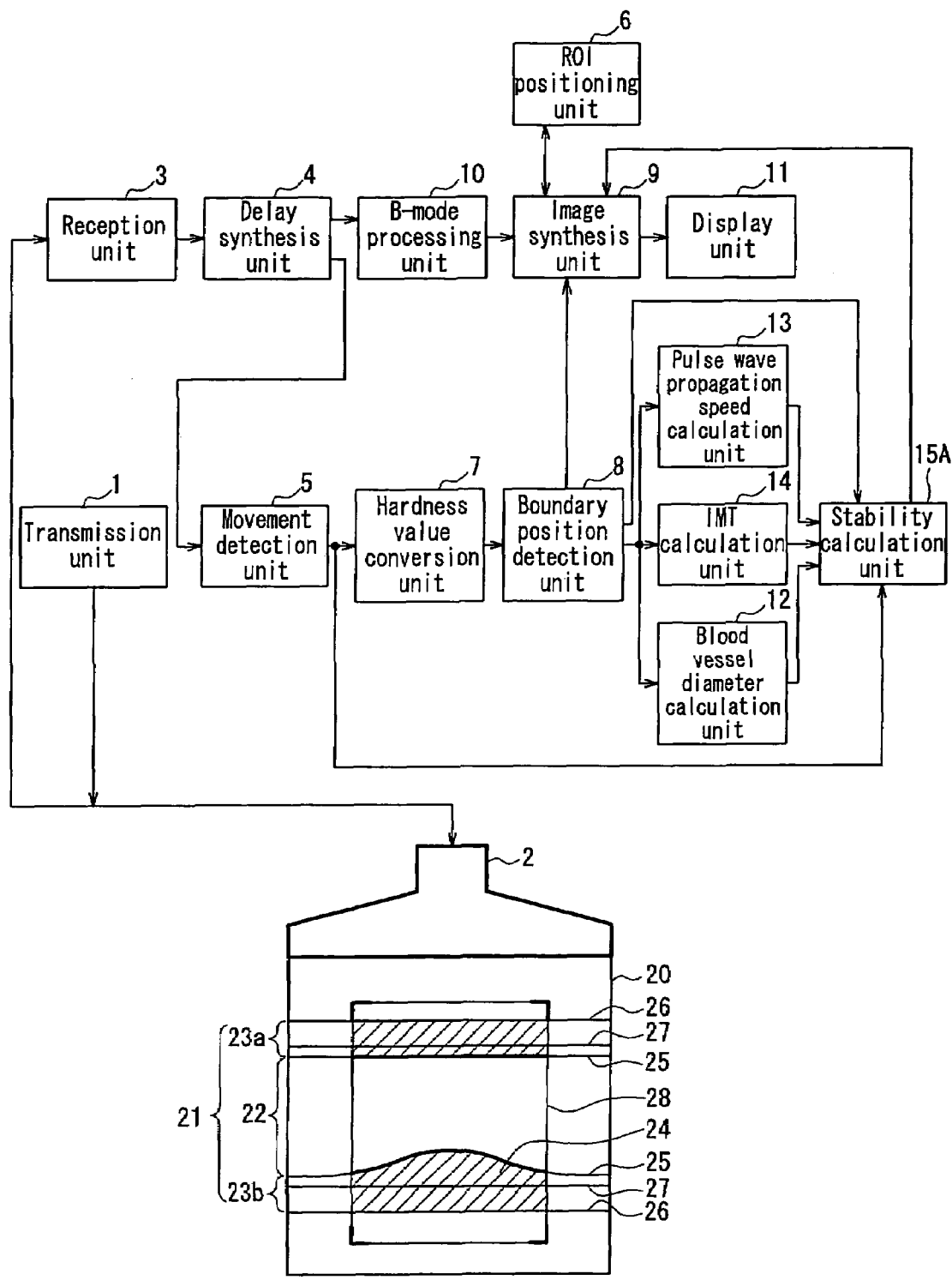
FIG. 4 is a block diagram showing a configuration of an ultrasonic diagnostic apparatus according to a second embodiment of the present invention.

FIG. 4 is a block diagram showing a configuration of an ultrasonic diagnostic apparatus according to a second embodiment. Components common to those of the ultrasonic diagnostic apparatus according to the first embodiment shown in FIG. 1 are denoted with the same reference numerals, and repeated descriptions will be omitted.

In the present embodiment, a stability judgment unit 15A has a different configuration from that of the stability judgment unit 15 in FIG. 1. The stability judgment unit 15A compares boundary positions and positions of the tunica media adjacent to each other in a direction traversing the blood vessel 21, the positions being detected by the boundary position detection unit 8, thereby judging the stability of the detection of the boundary positions and the positions of the tunica media by the boundary position detection unit 8.

Figure 5:
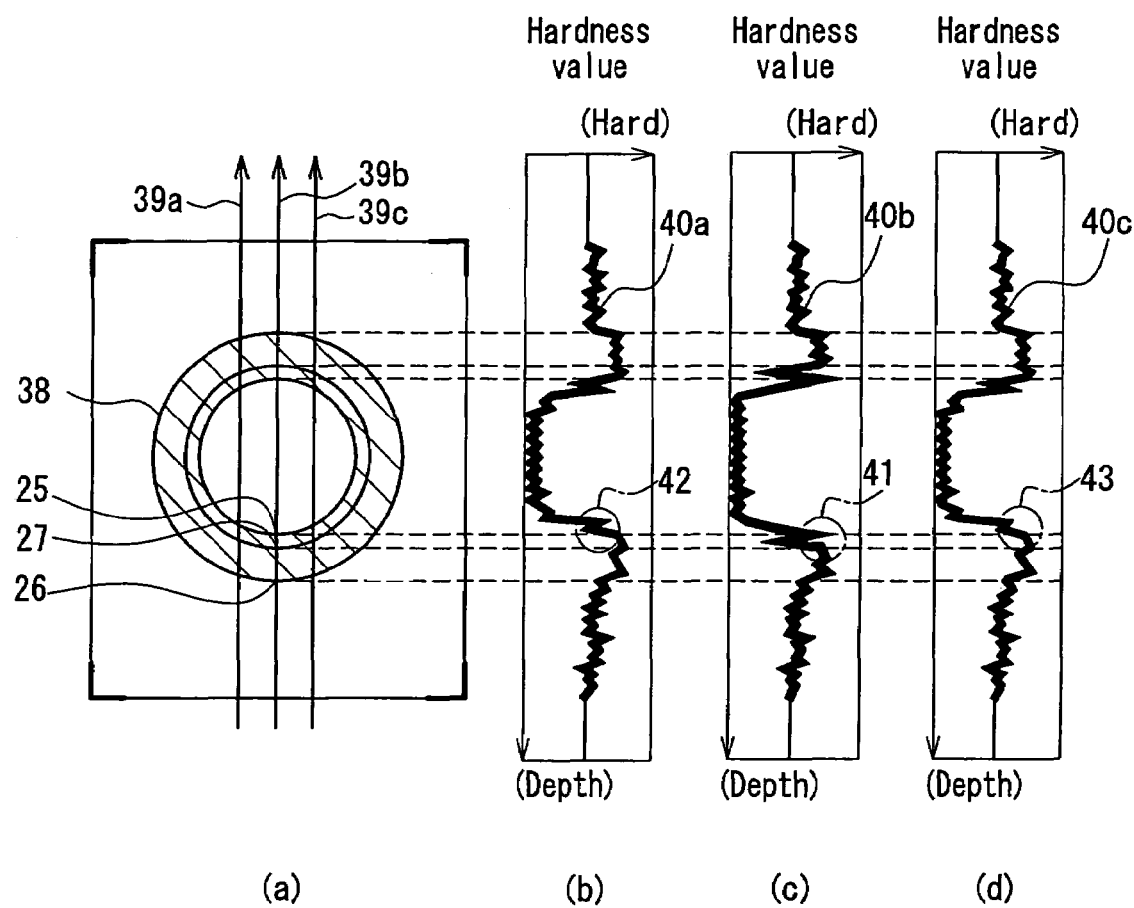
FIG. 5 is a schematic view for explaining an operation of the ultrasonic diagnostic apparatus shown in FIG. 4.

FIG. 5 is a schematic view for explaining an operation of the ultrasonic diagnostic apparatus according to the present embodiment. In FIG. 5, (a) shows a cross section 38 of the blood vessel. A measurement is performed such that three scanning lines 39a, 39b, and 39c pass through the cross section 38 of the blood vessel. In the Figure, (b) to (d) show hardness values 40a, 40b, and 40c measured by the scanning lines 39a, 39b, and 39c, respectively.

With respect to the hardness value 40b corresponding to the scanning line 39b that passes exactly through the center of the blood vessel, an ultrasonic echo signal has a clearer intensity difference because an ultrasonic signal impinges upon a wall surface and a film surface almost vertically. Thus, a clear peak waveform 41 for separating the tunica intima 25 and the tunica media 27 is obtained. On the other hand, with respect to the hardness values 40a and 40c corresponding to the scanning lines 39a and 39c, respectively, that do not pass exactly through the center of the blood vessel, the ultrasonic echo signal has an unclear intensity difference on the wall surface and the film surface, and waveforms 42 and 43 do not have their peaks. Consequently, it is difficult to separate the tunica intima 25 and the tunica media 27, and the IMT value cannot be obtained.

With the use of such characteristics of the hardness value, when the IMT value can be measured stably, it is possible to judge whether a path of the ultrasonic wave indicated by the scanning line is exactly through the center of the cross section of the blood vessel. Thus, the stability of a measurement itself by the ultrasonic diagnostic apparatus can be judged.

Further, the stability of the measurement can be judged by simultaneously referring to the results of the measurement of the IMT values in a plurality of regions in the direction traversing the blood vessel. Further, in combination with a comparison with the IMT value in the immediately preceding cycle or the like, the reliability of the measurement can be increased further.

As described above, the stability (constancy) of a measurement itself can be judged based on the fact that the center of the cross section of the blood vessel has to be captured at all times when the IMT value is measured.

Further, when an operator is notified of information indicating the stability (constancy) of a measurement itself in real time, the operator can judge during the measurement whether the present measurement result is reliable or not. Consequently, a measuring time can be made shorter.

INDUSTRIAL APPLICABILITY

According to the present invention, it is possible to provide the ultrasonic diagnostic apparatus that is capable of judging a state of stability of a measurement.

The invention claimed is:

1. An ultrasonic diagnostic apparatus, comprising:
    transmission means for transmitting at least one ultrasonic signal from a surface of a skin of a subject toward a blood vessel of the subject;
    reception means for receiving an ultrasonic echo reflected by the blood vessel and converting the ultrasonic echo into an electric signal to obtain the ultrasonic echo signal in a depth direction from the surface of the skin;
    movement detection means for analyzing a phase of the ultrasonic echo signal in a direction traversing the blood vessel to calculate a movement amount of a blood vessel wall composing the blood vessel;
    analysis means for analyzing a state of the blood vessel based on a difference of a track of movement of the blood vessel wall whose movement amount was calculated with respect to time;
    boundary position detection means for detecting a boundary position between a blood flow region and the blood vessel wall of the blood vessel based on a result of the analysis by the analysis means; and
    stability judgment means for comparing the boundary position detected by the boundary position detection means with a detection result in a previous heartbeat cycle, thereby judging stability of a measurement state.

2. The ultrasonic diagnostic apparatus according to claim 1, further comprising an ROI (Region of Interest) positioning means for positioning an ROI where the boundary position in the depth direction from the surface of the skin is to be detected by the boundary position detection means,
    wherein the ROI positioning means positions the ROI so that the ROI lies astride at least one of an anterior wall of the blood vessel wall on a side closer to the transmission means and a posterior wall of the blood vessel wall on a side farther from the transmission means.

3. The ultrasonic diagnostic apparatus according to claim 1, wherein the boundary position detection means detects the plurality of boundary positions in the depth direction from the surface of the skin,
    the apparatus further comprising a blood vessel diameter calculation means for calculating a diameter of the blood vessel based on the plurality of detected boundary positions.

4. The ultrasonic diagnostic apparatus according to claim 3, wherein the stability judgment means further compares the diameter of the blood vessel calculated by the blood vessel diameter calculation means with a calculation result in a previous cycle, thereby judging stability of a measurement state.

5. The ultrasonic diagnostic apparatus according to claim 1, wherein the boundary position detection means detects the boundary positions in the plurality of regions in the longitudinal direction of the blood vessel,
    the apparatus further comprising a pulse wave propagation speed calculation means for calculating a pulse wave propagation speed indicating a speed at which a pulse wave propagates, based on a variation with time in the plurality of boundary positions detected by the boundary position detection means.

6. The ultrasonic diagnostic apparatus according to claim 5, wherein the stability judgment means further compares the pulse wave propagation speed calculated by the pulse wave propagation speed calculation means with the pulse wave propagation speed calculated in a previous cycle, thereby judging stability of a result of the calculation of the pulse wave propagation speed.

7. The ultrasonic diagnostic apparatus according to claim 5, wherein the pulse wave propagation speed calculation means further calculates pulse wave propagation speeds in a plurality of adjacent regions in the longitudinal direction of the blood vessel, and the stability judgment means compares the pulse wave propagation speeds in the plurality of adjacent regions, thereby judging stability of a measurement state.

8. The ultrasonic diagnostic apparatus according to claim 1, wherein the boundary position detection means detects a boundary position between a tunica intima and the blood flow region of the blood vessel and a position of a tunica media of the blood vessel based on a hardness value of tissue in the depth direction, and the stability judgment means compares the boundary position and the position of the tunica media detected by the boundary position detection means with the boundary position and the position of the tunica media calculated a predetermined number or more of cycles prior to the present cycle, thereby judging stability of a measurement state.

9. The ultrasonic diagnostic apparatus according to claim 1, wherein the transmission means transmits a plurality of ultrasonic signals toward a plurality of regions in the longitudinal direction of the blood vessel, the boundary position detection means detects the boundary positions between the tunica intima and the blood flow region of the blood vessel and the positions of the tunica media of the blood vessel in a plurality of regions adjacent to each other in the longitudinal direction of the blood vessel, and the stability judgment means compares the boundary positions and the positions of the tunica media adjacent to each other that are detected by the boundary position detection means, thereby judging stability of a measurement state.

10. The ultrasonic diagnostic apparatus according to claim 1, further comprising an IMT (Intima-Media Thickness) calculation means for measuring an IMT, which is a thickness from the tunica intima to the tunica media, based on a variation with time in the boundary position between the tunica intima and the blood flow region of the blood vessel and a variation with time in the position of the tunica media of the blood vessel,
wherein the stability judgment means judges stability of a measurement state based on the IMT measured by the IMT calculation means.

11. The ultrasonic diagnostic apparatus according to claim 10, wherein the IMT calculation means calculates the IMT values in a plurality of regions adjacent to each other in the longitudinal direction of the blood vessel, and the stability judgment means compares the IMT values in the plurality of regions, thereby judging stability of a measurement state.

12. The ultrasonic diagnostic apparatus according to claim 1, further comprising display means for displaying the stability judged by the stability judgment means.

13. An ultrasonic diagnostic apparatus, comprising:
a transmission means for transmitting a plurality of ultrasonic signals from a surface of a skin of a subject toward a plurality of regions in a longitudinal direction of a blood vessel of the subject;
a reception means for receiving an ultrasonic echo reflected by the blood vessel and converting the ultrasonic echo into an electrical signal to obtain the ultrasonic echo signal in a depth direction from the surface of the skin:
a boundary position detection means for detecting a plurality of boundary positions in the longitudinal direction of the blood vessel; and
a stability judgment means for comparing the plurality of boundary positions detected by the boundary position detection means, thereby judging stability of a measurement state.

14. The ultrasonic diagnostic apparatus according to claim 13, wherein the boundary position detection means detects a boundary position between a tunica intima and a blood flow region of the blood vessel and a position of a tunica media of the blood vessel based on a hardness valve of tissue in the depth direction, and the stability judgment means compares the boundary position and the position of the tunica media detected by the boundary position detection means with the boundary position and the position of the tunica media calculated a predetermined number or more of cycles prior to the present cycle, thereby judging stability of a measurement state.

15. The ultrasonic diagnostic apparatus according to claim 13, wherein the boundary position detection means detects boundary positions between a tunica intima and a blood flow region of the blood vessel and positions of a tunica media of the blood vessel in a plurality of regions adjacent to each other in the longitudinal direction of the blood vessel, and the stability judgment means compares the boundary positions and the positions of the tunica media adjacent to each other that are detected by the boundary position detection means, thereby judging stability of a measurement result.

16. The ultrasonic diagnostic apparatus according to claim 13, further comprising an IMT (Intima-Media Thickness) calculation means for measuring an IMT, which is a thickness from a tunica intima to a tunica media, based on a variation with time in a boundary position between the tunica intima and a blood flow region of the blood vessel and a variation with time in a position of the tunica media of the blood vessel,
wherein the stability judgment means judges stability of a measurement state based on the IMT measured by the IMT calculation means.

17. The ultrasonic diagnostic apparatus according to claim 16, wherein the IMT calculation means calculates IMT values in a plurality of regions adjacent to each other in the longitudinal direction of the blood vessel, and the stability judgment means compares the IMT values in the plurality of regions, thereby judging stability of a measurement state.

18. The ultrasonic diagnostic apparatus according to claim 13, further comprising display means for displaying the stability judged by the stability judgment means.

* * * * *